(12) United States Patent
Llaudet Carles et al.

(10) Patent No.: US 11,382,867 B2
(45) Date of Patent: Jul. 12, 2022

(54) APOMORPHINE-PALMITIC ACID COCRYSTAL SOLID PARTICLE CRYSTALLINE FORM

(71) Applicant: LEUKOS BIOTECH, S. L., Barcelona (ES)

(72) Inventors: Enrique Llaudet Carles, Barcelona (ES); Nicolas Tesson, L'Hospitalet de Llobregat (ES); Montserrat Trilla Castaño, Barcelona (ES)

(73) Assignee: LEUKOS BIOTECH, S. L., Barcelona (ES)

( * ) Notice: Subject to any disclaimer, the term of this patent is extended or adjusted under 35 U.S.C. 154(b) by 106 days.

(21) Appl. No.: 16/962,585

(22) PCT Filed: Jan. 15, 2019

(86) PCT No.: PCT/EP2019/050922
§ 371 (c)(1),
(2) Date: Jul. 16, 2020

(87) PCT Pub. No.: WO2019/141673
PCT Pub. Date: Jul. 25, 2019

(65) Prior Publication Data
US 2020/0405648 A1  Dec. 31, 2020

(30) Foreign Application Priority Data
Jan. 18, 2018  (EP) .................... 18382023

(51) Int. Cl.
*A61K 31/473* (2006.01)
*A61K 9/51* (2006.01)
*A61K 9/00* (2006.01)
*A61K 9/10* (2006.01)

(52) U.S. Cl.
CPC .............. *A61K 9/51* (2013.01); *A61K 9/0021* (2013.01); *A61K 9/10* (2013.01); *A61K 31/473* (2013.01)

(58) Field of Classification Search
CPC .................................................. A61K 31/473
See application file for complete search history.

(56) References Cited

FOREIGN PATENT DOCUMENTS

| WO | 0214279 A1 | 2/2002 |
| WO | 0239879 A2 | 5/2002 |
| WO | 2004082630 A2 | 9/2004 |
| WO | 2015197839 A1 | 12/2015 |
| WO | 2016103262 A2 | 6/2016 |

OTHER PUBLICATIONS

Schultheiss et al. "Pharmaceutical cocrystals and their physicochemical properties." Crystal growth and design 9.6 (2009): 2950-2967.
International Search Report and Written Opinion in Corresponding PCT Application No. PCT/EP2019/050922 dated Jul. 25, 2019. 8 pages.
International Preliminary Report on Patentability in Corresponding PCT Application No. PCT/EP2019/050922 dated Jul. 21, 2020. 6 pages.

*Primary Examiner* — Benjamin J Packard
(74) *Attorney, Agent, or Firm* — Dechert LLP (57) ABSTRACT

A pharmaceutical composition comprising apomorphine (APO) in a solid crystalline form, wherein the solid crystalline form is an APO·palmitic acid cocrystal solid particle crystalline form.

15 Claims, 6 Drawing Sheets

1H-NMR of Form O

Figure 3:

XRPD of Form P

Figure 4:

The 1H-NMR spectrum of Form P shows approximately a 1:7 molar ratio (APO FB:palmitic acid)

1H-NMR of Form P

Figure 5:

Comparison of kinetic solubility profile of the different studied crystalline APO salts

Figure 6:

APOMORPHINE-PALMITIC ACID COCRYSTAL SOLID PARTICLE CRYSTALLINE FORM

CROSS-REFERENCE TO RELATED PATENT APPLICATIONS

This application is a U.S. National Stage Application under 35 U.S.C. § 371 of International Patent Application No. PCT/EP2019/050922, filed Jan. 15, 2019, which claims the benefit of priority of European Patent Application number 18382023.2 filed Jan. 18, 2018, both of which are incorporated by reference in their entireties. The International Application was published on Jul. 25, 2019, as International Publication No. WO 2019/141673 A1.

FIELD OF THE INVENTION

The present invention relates to a pharmaceutical composition comprising apomorphine (APO) in a solid crystalline form, wherein the solid crystalline form is an APO·palmitic acid cocrystal solid particle crystalline form.

BACKGROUND ART

Apomorphine (APO) is a commercial available medical drug with the chemical formula $C_{17}H_{17}NO_2$ and structure:

Apomorphine (APO) has been described for treatment of different medical indications for instance:
WO2015/197839A1: leukemia such as acute myeloid leukemia (AML);
WO2016/103262A2: Parkinson's disease;
WO02/39879A2: sexual dysfunction in a patient taking antidepressant medication;
WO2004/082630A2: neurological function of an individual who has a brain injury.

Apomorphine hydrochloride (HCl) is a salt present in commercially available medical products (e.g. APO-Go® PFS or Apokyn®).

A common side effect of administering apomorphine hydrochloride by e.g. subcutaneous injection is e.g. the development of subcutaneous nodules at the injection site, which can become infected, necessitating treatment or surgical involvement.

In relation to this problem—above discussed WO2016/103262A2 describes an alternative solid form of apomorphine, which is e.g. an alcohol solvate crystal of apomorphine free base, wherein the solvate forming solvent is ($C_1$-$C_8$) alkanol, preferably isopropanol (IPA—i.e. a solid crystalline form of apomorphine-IPA.

Palmitic acid (hexadecanoic acid in IUPAC nomenclature) is a fatty acid found with the chemical formula $CH_3(CH_2)_{14}COOH$.

Palmitate is the salt and ester of palmitic acid.
A herein relevant synonyms name may e.g. be palmitoate.

Beside apomorphine hydrochloride, above discussed WO2015/197839A1 and WO2004/082630A2 provide a list of other possible suitable pharmaceutically acceptable salts—palmitic acid (or synonyms like palmitate or palmitoate) is not mentioned in the lists of these two WO documents.

As discussed in the review article of Schultheiss et al. ("Pharmaceutical Cocrystals and Their Physicochemical Properties"; Crystal Growth & Design, Vol. 9, No. 6,2009, p. 2950-2967)—solid-state chemists call upon a variety of different strategies when attempting to alter the chemical and physical solid-state properties of active pharmaceutical ingredients (APIs), namely, the formation of salts, polymorphs, hydrates, solvates, and cocrystals.

Salt formation is one of the primary solid-state approaches used to modify the physical properties of APIs, and it is estimated that over half of the medicines on the market are administered as salts. However, a limitation within this approach is that the API must possess a suitable (basic or acidic) ionizable site. In comparison, cocrystals (multicomponent assemblies held together by freely reversible, noncovalent interactions) offer a different pathway, where any API regardless of acidic, basic, or ionizable groups, could potentially be cocrystallized.

Above discussed WO02/39879A2 also provides a long list of suitable pharmaceutically acceptable salts and mentions palmitoate (see page 5, line 16).

However, in all herein relevant experimental work of this WO document was used apomorphine hydrochloride and a palmitic acid based salt is simply mentioned in a list i.e. a palmitic acid based salt is not a preferred salt.

Alternatively expressed, by reading this WO document the skilled person has in practice no motivation to use any other solid form than apomorphine·HCl—one reason for this is that apomorphine·HCl is used in all herein relevant experimental work of this WO document.

The term "cocrystal" is not mentioned in this WO document—i.e. it is evident that this document does not disclose an APO·palmitic acid cocrystal solid particle crystalline form.

In summary, none of above mentioned prior art documents describe or suggest that apomorphine (APO) palmitic acid (APO·palmitic acid) could be a preferred pharmaceutically acceptable solid form.

Further, since APO·palmitic acid solid form is not used in any herein relevant experimental work of the prior art—none of above mentioned prior art documents describe an experimental method for actually making a pharmaceutically relevant APO·palmitic acid crystalline solid form.

SUMMARY OF THE INVENTION

The problem to be solved by the present invention is to provide a novel composition of apomorphine (APO) with relevant improved pharmacological properties.

The present invention may be seen as based on that the present inventors identified that APO·palmitic acid cocrystal solid particle crystalline form has a number of commercial relevant surprisingly good and advantageous pharmacological properties.

As discussed herein, based on the technical information of the present application—the skilled person understands that an APO·palmitic acid solid form as described herein may be used to make relevant a pharmaceutical composition (e.g. a slow release suspension for e.g. injection subcutaneous injection) for treatment of different medical indications—such as e.g. acute myeloid leukemia.

The data of Example 5 herein demonstrates that an APO·palmitic solid form of the invention has a surprising significant slower solubility rate in aqueous media as compared to any of the other tested solid forms.

Figure 5:
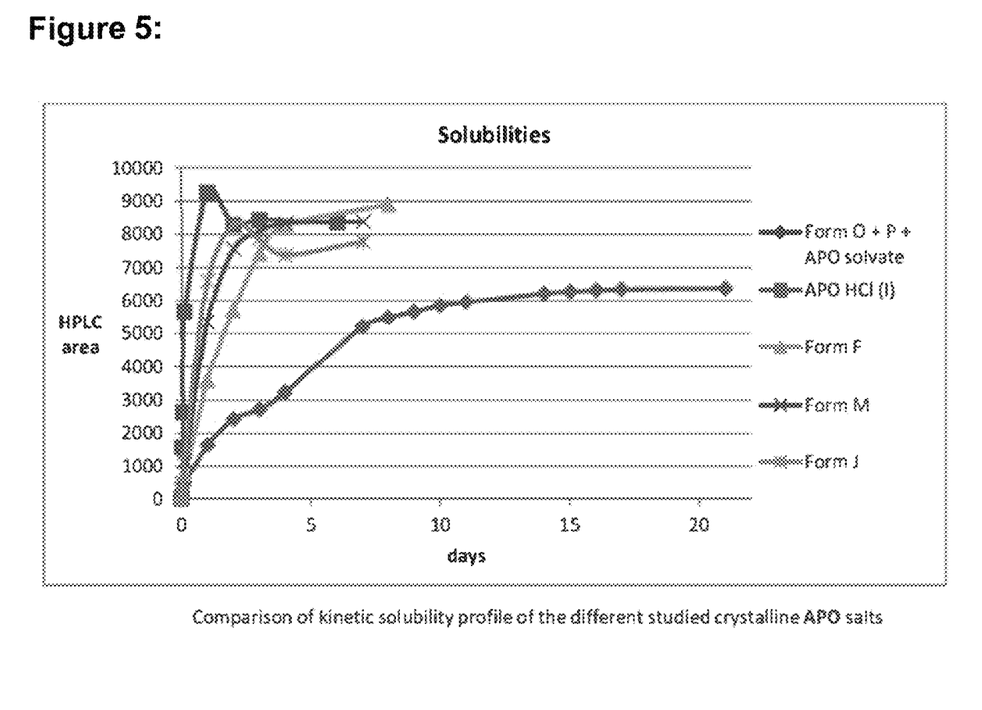
FIG. 5 shows the result of the comparison of kinetic solubility profile of the different studied crystalline APO salts—it demonstrates that an APO·palmitic solid form of the invention has a surprising significant slower solubility rate in aqueous media as compared to any of the other tested salts. The mentioned "APO solvate" in the figure was a very minor (w/w) impurity.

As can be seen in FIG. 5 herein other tested APO solid forms (e.g. benzoic acid salt, adipic acid salt, sulfuric acid salt) have a relatively small slower solubility rate as compared to apomorphine hydrochloride (apomorphine·HCl) salt i.e.—it is only APO·palmitic solid form that has a significant slower solubility rate.

From a herein relevant commercial pharmaceutical point of view, it may be said that the relatively small slower solubility rate of other tested APO solid forms (e.g. benzoic acid salt, adipic acid salt, sulfuric acid salt) is not enough in order to e.g. make a relatively simple clinical relevant slow-release suspension of APO solid form in an aqueous media (e.g. water as such or e.g. a standard used buffered aqueous media comprising e.g. Tween (polysorbate—e.g. Tween 20)).

The present inventors initially tested other APO solid forms (e.g. benzoic acid salt, adipic acid salt, sulfuric acid salt—which prima facie may be considered standard pharmaceutically acceptable salts) and could in principle have given up, since the data demonstrated what skilled person prima facie objectively could have believed—i.e. that the other tested salts did not have a sufficient significant slower solubility.

However, the present inventors continued and surprisingly identified that APO·palmitic acid solid crystalline form as described herein has a herein commercial pharmaceutical relevant significant slower solubility rate in aqueous media.

As discussed herein, the fact that APO·palmitic acid solid crystalline form has such a significant slower solubility rate in aqueous media gives the possibility of making e.g. a relatively simple slow-release suspension of APO solid form in an aqueous media that could be administrated to patients (e.g. via subcutaneous injection) less frequently (e.g. once every 2 days or may be even less frequently.)

The data of Example 4 herein demonstrates that an APO·palmitic solid form of the invention is stable, since it is stable over 1 week under accelerated conditions.

A further herein relevant advantage is that an APO·palmitic solid form of the invention is believed to have a low toxicity a reason for this relates to the very low toxicity of palmitic acid as such.

Based on the technical information of the present application the skilled person understands that an APO·palmitic acid solid form as described herein may advantageous be used to make numerous different pharmaceutical compositions of interest—e.g. a tablet, a gel, a suspension etc.

Accordingly, a first aspect of the invention relates to a pharmaceutical composition comprising pharmaceutically acceptable excipient(s) and comprising apomorphine (APO) in a solid crystalline form, wherein the solid crystalline form is an APO·palmitic acid cocrystal solid particle crystalline form.

In the present context, the term "cocrystal" of the first aspect is well known to the skilled person and based on the general knowledge of the skilled person and the technical information herein the skilled person can routinely determine if a solid form is a cocrystal solid form of the first aspect.

The above discussed review article of Schultheiss et al. ("Pharmaceutical Cocrystals and Their Physicochemical Properties"; Crystal Growth & Design, Vol. 9, No. 6, 2009, p. 2950-2967) provides an according to the art definition of the term "cocrystal"—the term "cocrystal" of the first aspect is understood in accordance with the definition of the Schultheiss et al. article. In relation to the definition of the term "cocrystal" reads the Schultheiss et al. article: "multicomponent assemblies held together by freely reversible, noncovalent interactions"; "(1) An API, neutral (example 1, FIG. 2), or ionic form (example 2, FIG. 2, or a zwitterion), along with a neutral coformer, held together through non-covalent, freely reversible interactions".

Depending on the pharmaceutical composition of interest the skilled person knows numerous possible suitable pharmaceutically acceptable excipients—i.e. it is herein not considered necessary to discuss this in great details.

For instance, if the pharmaceutical composition is a suspension a suitable pharmaceutically acceptable excipient could e.g. be polysorbate (e.g. polysorbate 20=Tween 20), which could be a suitable excipient present in a suitable percentage in e.g. an aqueous medium.

If the pharmaceutical composition is a tablet—suitable pharmaceutically acceptable excipients could e.g. be diluents, binders (e.g. methyl cellulose), lubricants, etc.

An antioxidant agent such as e.g. ascorbic acid is also an example of pharmaceutically acceptable excipient.

Further, in some cases may water also be considered a pharmaceutically acceptable excipient.

It is routine work for the skilled person to obtain a pharmaceutical composition as described herein—i.e. it is herein not considered necessary to discuss this in great details.

For instance, if the pharmaceutical composition is a suspension it may be obtained by suspending the APO·palmitic acid cocrystal solid particle crystalline form as described herein in a suitable media (e.g. aqueous media) in order to get a suspension.

If the pharmaceutical composition is a tablet the suitable pharmaceutically acceptable excipients (e.g. diluents, binders, lubricants etc) may be mixed with the APO·palmitic acid cocrystal solid particle crystalline form as described herein and a tablet may be prepared by e.g. use of standard molding and/or compression techniques.

It is also routine work to make other possible suitable pharmaceutical compositions, such as e.g. gels etc.

A second aspect of the invention relates to a pharmaceutical composition of the first aspect and/or embodiment thereof for use as a medicament.

A third aspect of the invention relates to a pharmaceutical composition of the first aspect and/or embodiment thereof for use in the treatment of:

leukemia (preferably acute myeloid leukemia (AML));
Parkinson's disease;
sexual dysfunction (preferably in a patient taking antidepressant medication);
neurological function (preferably of an individual who has a brain injury); or
solid tumors
in a human person.

The present disclosure also provides methods to treat, prevent, or ameliorate the symptoms of above-mentioned diseases.

A fourth aspect of the invention relates to a method for making an APO·palmitic acid cocrystal solid particle crystalline form comprising the steps:
(i): suspending apomorphine free base (APO FB) and palmitic acid in a suitable medium (preferably toluene) to get a suspension;
(ii): heating to get a solution;

(iii): cooling to get precipitation; and
(iv): further steps (including e.g. filtering) to obtain the APO·palmitic acid cocrystal solid particle crystalline form.

Embodiment of the present invention is described below, by way of examples only.

As understood by the skilled person in the present context, a combination of a preferred embodiment with another preferred embodiment may be seen as an even more preferred embodiment.

DRAWINGS

FIG. 5.

FIG. 6.

DETAILED DESCRIPTION OF THE INVENTION

First aspect—composition comprising APO·palmitic acid cocrystal solid particle crystalline form.

As discussed above, a first aspect of the invention relates to a pharmaceutical composition comprising pharmaceutically acceptable excipients and comprising apomorphine (APO) in a solid crystalline form, wherein the solid crystalline form is an APO·palmitic acid cocrystal solid particle crystalline form.

The cocrystal may preferably be an ionic cocrystal.

Preferably, the pharmaceutical composition is a composition, wherein at least 20% (preferably at least 40%, more preferably at least 60%, even more preferably at least 80% and most at least 90%) of APO of the composition (w/w of APO as such) is an APO·palmitic acid cocrystal solid particle crystalline form.

It may be most preferred that the composition is a composition, wherein at least 97% of APO of the composition (w/w of APO as such) is an APO·palmitic acid cocrystal solid particle crystalline form.

As understood by the skilled person in the present context the term "w/w of APO as such" relates to that the w/w percentage is calculated based on the APO as such i.e. not including the weight of palmitic acid or the weight of e.g. HCl if the composition e.g. should comprise some amounts of apomorphine·HCl.

It is routine work for the skilled person to determine if a composition of interest is a composition wherein e.g. "at least 20% of APO in solid crystalline form of the composition (w/w of APO as such) is an APO·palmitic acid solid crystalline form".

In a preferred embodiment, the average particle size of the APO·palmitic acid cocrystal solid particle crystalline form of the first aspect is an average particle size of from 100 nm to 10 μm.

It is routine work for the skilled person to measure the average particle size preferably it is done by laser diffraction.

As known in the art, laser diffraction measures particle size distributions by measuring the angular variation in intensity of light scattered as a laser beam passes through a dispersed particulate sample. Large particles scatter light at small angles relative to the laser beam and small particles scatter light at large angles. The angular scattering intensity data is then analyzed to calculate the size of the particles responsible for creating the scattering pattern, using e.g. the Mie theory of light scattering. The particle size is reported as a volume equivalent sphere diameter.

In working Examples herein were the APO·palmitic obtained in two different solid particle crystalline forms—one is termed Form O (ratio APO·palmitic acid is around 1:2) and the other is termed Form P (ratio APO·palmitic acid is approximately 1:7).

Without being limited to theory, the present inventors do not believe there is a significant difference between Form O and Form P in relation to herein relevant advantageous properties such as e.g. the kinetic solubility (see e.g. Example 5).

Accordingly, APO·palmitic acid may be obtained in different solid forms with different ratios of ratio APO·palmitic. Based on the teaching herein it is believed that there is prima facie no reason to believe that it should not be possible to obtain APO·palmitic with different rations than herein exemplified.

In a preferred embodiment, the APO·palmitic acid cocrystal solid particle crystalline form of the first aspect is a form, wherein the ratio APO·palmitic acid is a ratio from 1:1 to 1:15, more preferably a ratio from 1:2 to 1:15 (such as e.g. a ratio from 1:1 to 1:10 or 1:2 to 1:10 or 1:1 to 1:8 or 1:2 to 1:8).

Form P (ratio APO·palmitic acid is approximately 1:7) comprises more palmitic acid than Form O (ratio APO·palmitic acid is around 1:2) and it may be preferred to have less palmitic acid.

Accordingly, in an even more preferred embodiment the APO·palmitic acid salt solid particle crystalline form of the first aspect is a form, wherein the ratio APO·palmitic acid is a ratio from 1:1 to 1:3 most preferably the ratio APO·palmitic acid is a ratio 1:2.

Figure 1:
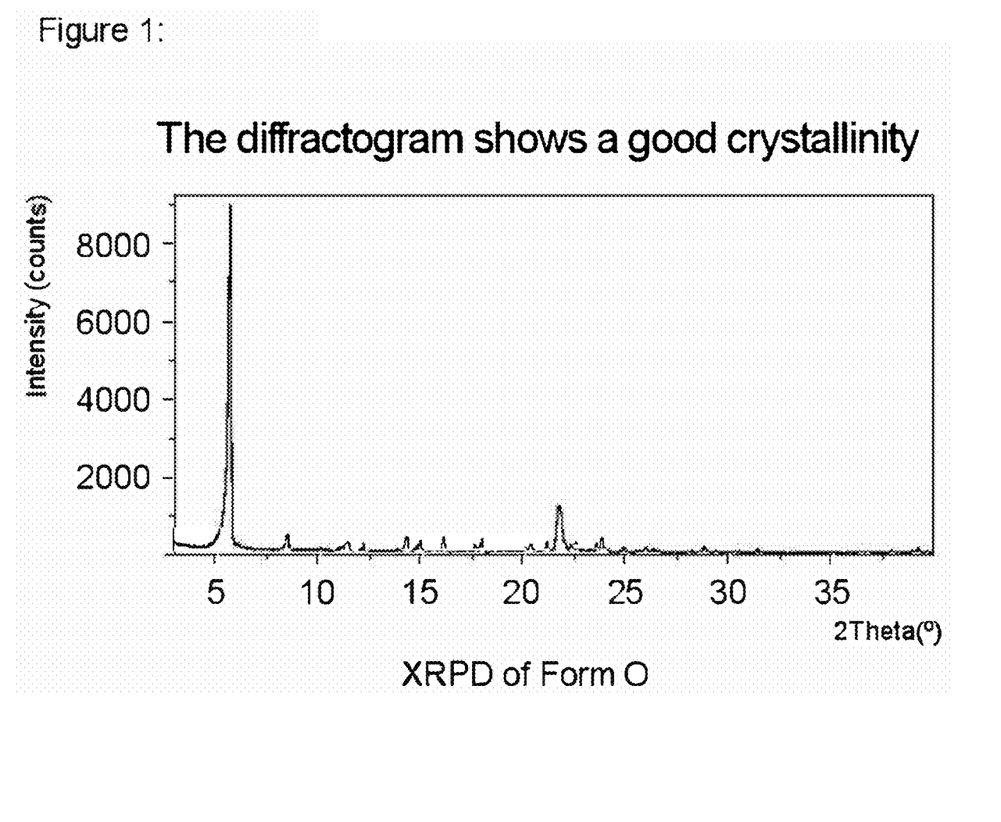
FIG. 1: The X-ray Powder Diffraction (XRPD) diffractogram of Form O APO·palmitic acid. For further details see Example 2 herein.

The X-ray Powder Diffraction (XRPD) diffractogram of Form O APO·palmitic acid is shown in FIG. 1—as discussed below, the cocrystal Form O of the present invention is characterized by having an X-ray powder diffractogram that comprises characteristic peaks at 5.8, 8.6 and 11.5±0.3 degrees 2 theta at a Cu-Kα radiation, λ=1.5406 Å. The cocrystal Form O of the present invention is characterized by having an X-ray powder diffractogram that comprises further characteristic peaks at 16.2 and 18.1±0.3 degrees 2 theta at a Cu-Kα radiation, λ=1.5406 Å. As discussed herein—the XRPD diffractogram of Form P (FIG. 3) comprises characteristic peaks different from the characteristic peaks of Form O.

In a preferred embodiment, APO·palmitic acid solid particle crystalline form is Form O with X-ray Powder Diffraction (XRPD) diffractogram corresponding to the XRPD diffractogram of FIG. 1, where characteristic peaks include characteristic peaks at 5.8, 8.6 and 11.5±0.3 degrees 2 theta at a Cu-Kα radiation, λ=1.5406 Å.

The APO·palmitic acid salt solid particle crystalline form may be cocrystal Form P, which is characterized by having an X-ray powder diffractogram that comprises characteristic peaks at 4.1, 6.2 and 10.3±0.3 degrees 2 theta at a Cu-Kα radiation, λ=1.5406 Å.

As known in the art, different XRPD diffractograms of the same crystalline form may have different peak intensities—i.e. same characteristic peaks just with different peak intensities.

Accordingly, the term "corresponding" in relation to "the XRPD diffractogram of FIG. 1" should be understood according to the art—i.e. as a XRPD diffractogram with same characteristic peaks. Based on the XRPD diffractogram of FIG. 1 is it routine work for the skilled person to determine if a APO·palmitic crystalline form of interest is Form O as discussed herein.

The pharmaceutical composition may e.g. be a tablet, a gel, a suspension, a solution, a liposome, or encapsulated in polymers.

In a preferred embodiment, the pharmaceutical composition is a suspension—preferably, wherein the APO·palmitic acid cocrystal solid particle crystalline form is suspended in an aqueous medium.

The aqueous medium may e.g. be water or more preferably a buffered aqueous media comprising e.g. Tween (polysorbate—e.g. Tween 20).

Preferably the suspension is a suspension for subcutaneous injection.

As discussed in Example 5 herein—the kinetic solubility study of selected APO forms was performed at 37° C. in water in the presence of ascorbic acid (0.05% w/w) to avoid degradation and compared with APO HCl (I). In order to simulate subcutaneous injections, the solid was introduced in a dialysis bag. The kinetic profile of all the tested APO forms indicates a slower APO release in the medium than that of APO HCl (I). However, the best profile was obtained with the APO·palmitic acid solid form of the invention.

Accordingly, in a preferred embodiment the pharmaceutical composition as described herein is a pharmaceutical composition, wherein the kinetic solubility at 37° C. in water in the presence of ascorbic acid (0.05% w/w) of the APO·palmitic acid solid form is slower than for APO HCl tested under the same conditions.

Preferably, the kinetic solubility of the APO·palmitic form after 3 days is at least 20% (more preferably at least 30%, even more preferably at least 40% and even more preferably at least 50%) slower than for APO HCl.

The solubility tests are preferably performed as described in Example 5.

Second Aspect—Use as a Medicament.

As discussed above, a second aspect of the invention relates to a pharmaceutical composition of the first aspect and/or embodiment thereof for use as a medicament.

It is routine work for the skilled person to prepare a herein relevant medicament of interest i.e. it is herein not considered necessary to discuss this in great details.

Third Aspect—Use in the Treatment of Different Diseases.

As discussed above, a third aspect of the invention relates to a pharmaceutical composition of the first aspect and/or embodiment thereof for use in the treatment of:
leukemia (preferably acute myeloid leukemia (AML);
Parkinson's disease;
sexual dysfunction (preferably in a patient taking antidepressant medication);
neurological function (preferably of an individual who has a brain injury); or
solid tumors in a human person.

Preferably, the pharmaceutical composition is used for the treatment of:
leukemia (preferably acute myeloid leukemia (AML); or
Parkinson's disease.

Alternatively, the invention relates to the use of a pharmaceutical composition of the first aspect and/or embodiment thereof for the preparation of a medicament for the treatment of the above-mentioned diseases.

Alternatively, the invention relates to a method for treating the above mentioned diseases comprising administering a pharmaceutical composition of the first aspect and/or embodiment thereof to a subject in need thereof.

As discussed herein, the fact that APO·palmitic acid solid crystalline form has a significant slower solubility rate in aqueous media gives the possibility of making e.g. relatively simple slow-release suspension of APO solid form in an aqueous media that could be administrated to patients (e.g. via subcutaneous injection) less frequently (e.g. once every 2 days or may be even once every year).

As known in the art—slow-release dosage form may e.g. be referred to as sustained-release dosage form and it is not a so-called immediate-release dosage form.

Accordingly, it may be preferred that the treatment of the third aspect is a treatment, wherein the pharmaceutical composition is administrated to the human person over a period within the range of from every two days to every year (such as a period within the range of from every two days to every second week or a period within the range of from every fourth days to every 9 days).

As understood by the skilled person a period within the range of from every two days to every year means that the pharmaceutical composition is e.g. not administrated every day.

In a preferred embodiment, the pharmaceutical composition is used for the treatment of leukemia (preferably acute myeloid leukemia (AML), where it is preferred that the pharmaceutical composition is a suspension (preferably wherein the suspension is a suspension for subcutaneous injection) and it is preferred that the pharmaceutical composition is administrated to the human person over a period within the range of from every two days to every year (such as a period within the range of from every two days to every second week or a period within the range of from every fourth days to every 9 days).

Fourth aspect a method for making an APO·palmitic acid cocrystal.

As discussed above, a fourth aspect of the invention relates to a method for making an APO·palmitic acid cocrystal solid particle crystalline form comprising the steps:

(i): suspending apomorphine free base (APO FB) and palmitic acid in a suitable medium (preferably toluene) to get a suspension;

(ii): heating to get a solution;

(iii): cooling to get precipitation; and (iv): further steps (including e.g. filtering) to obtain the APO·palmitic acid cocrystal solid particle crystalline form.

As discussed in working Examples herein—particular good results were obtained when using toluene—accordingly, it is preferred that the suitable medium in step (i) is toluene.

Based on the technical teaching herein (see e.g. Examples) it is routine work for the skilled person to optimize the method—e.g. optimizing the heating and/or cooling steps.

It may be preferred that the heating in step (ii) is done at a temperature from 40° C. to 60° C. The cooling may preferably be performed slowly.

EXAMPLES

Example 1: Preparation of Apomorphine Free Base (APO FB)

APO FB (apomorphine free base) was prepared based on the procedure described in WO2016/103262 (Example 1, page 18): preparation of apomorphine free base by aqueous method.

Experimental procedure APO HCl (I) (5.5 g, 17.6 mmol) and aq. 0.1% w/w $Na_2S_2O_5$ (385 mL, 70 V) were added to a round-bottomed flask, under $N_2$ atmosphere, resulting in a clear solution ($Na_2S_2O_5$ was used to avoid oxidation of free APO). Subsequently 1N $Na_2CO_3$ (55 mL, 26.4 mmol, 1.5 eq), previously purged with $N_2$, was added during 5 minutes. Immediate precipitation was observed. The mixture was subjected to continuous stirring, under $N_2$ atmosphere, at 0-5° C. for 30 minutes. Then, it was filtered in a sintered funnel (porosity 3) under $N_2$ atmosphere and the solids were washed with cold water (2×11 mL, 2×2 V).

In some preparations the wet solid is used to obtain the corresponding salt.

When it was needed, the solids were dried under vacuum overnight ($CaCl_2$ was used to aid the drying process) leading to APO FB (4.7 g; yield 99%, white solid).

Experimental Procedure—APO FB (E85-2-128)
1. Add APO HCl (I) (7.50 g, 23.98 mmol) and $Na_2S_2O_5$ aq. (0.1% w/w, 530 mL, 70 V) ($Na_2S_2O_5$ was used to avoid oxidation of the compound) to a round-bottomed flask, under $N_2$ atmosphere.
Clear solution
2. Add 1N $Na_2CO_3$ (75 mL, 35.38 mmol, 1.5 eq), previously purged with $N_2$.
Immediate precipitation observed
3. Stir for 30 min at 0-5° C.
4. Filter in a sintered funnel (porosity 3) under $N_2$ atmosphere.
5. Wash the solids with cold water (2×15 mL, 2×2 V).
6. Dry at 40° C. under vacuum (approx. 1 mbar) overnight in the presence of $CaCl_2$ ($CaCl_2$ used to aid the drying process) to afford APO FB (6.20 g, yield 97%) as a white-greenish solid.

Example 2: Experimental Procedure for "Form O" Preparation: Apo-Palmitic Acid (1:2)

Preparation of Form O by Crystallization in Toluene at 2 g Scale with Magnetic Stirring (E85-2-125)

In a 100 mL round-bottomed flask, APO FB (1.97 g, 7.37 mmol) and palmitic acid (3.46 g, 13.49 mmol, 1.8 eq) were suspended in toluene (30 mL, 15 V). The mixture was heated to 50° C. (clear solution) and stirred at this temperature for 1.5 h (until turbidity was observed). It was cooled slowly to RT and seeded with the impurity (E85-2-046B). The slurrying was heated to 60° C. and then cooled to 50° C. No clear solution was reached and the solid was filtered with a sintered funnel (porosity 3). The mother liquors (clear solution) were slowly cooled to RT overnight. The solid was filtered with a sintered funnel (porosity 3), washed with toluene (2×4 mL, 2×2 V) and dried under vacuum (approx. 1 mbar, RT, 5 h) giving Form O (4.04 g, 77%)1 as a white solid.

Form O Preparation Process (E85-2-130)
1. Add APO FB (6.20 g, 23.191 mmol, E85-2-128), palmitic acid (10.7 g, 41.744 mmol, 1.8 eq) and toluene (93 mL, 15V) to a 250 mL reactor equipped with mechanic stirrer and a thermometer, at RT.
Brownish suspension
2. Heat to 50° C. (internal temperature) and stir for 1 h.
Slight turbid dark solution
3. Cool slowly to RT.
Precipitation at 27° C.
4. Heat to 50° C. and stir for 1 h.
Slight turbid dark solution
5. Filter the turbid solution with a sintered funnel (porosity 3).
A dark solution is obtained
6. Cool slowly to RT.
7. Seed with Form O (E85-2-125) at 39° C., 34° C. and 29° C. (internal temperature).
Turbidity observed at 29° C.
8. Stir at RT overnight under continuous stirring.
9. Filter the solid with a sintered funnel (porosity 2) and wash with toluene (2×12 mL; 2 V).
10. Dry the product at RT under vacuum (approx. 1 mbar) overnight giving Form O (13.2 g, 81%) as an off-white solid.
Characterization of Form O (E85-2-130)

X-ray power Diffraction (XRPD) measurements were performed at ambient conditions on a PANa-lytical X'Pert PRO θ-θ diffractometer of 240 mm of radius in reflection geometry, equipped with Cu Kα radiation and a PIXcel detector, operated at 45 kV and 40 mA. Each sample was mounted on a zero-background silicon holder and allowed to spin at 0.25 rev/s during the data collection. The measurement angular range was 3.0-40.0° (2θ) with a step size of 0.013° and a scanning speed 0.328°/s (10.20 s/step) for Form P 3.0-40.0° (2θ) with a step size of 0.013° and a scanning speed 0.082°/s (40.80 s/step) for Form O.

The XRPD diffractogram of Form O (E85-2-130) is shown in FIG. 1—it shows a good crystallinity.

The cocrystal Form O of the present invention is characterized by having an X-ray powder diffractogram that comprises characteristic peaks at 5.8, 8.6 and 11.5±0.3 degrees 2 theta at a Cu-Kα radiation, λ=1.5406 Å. The cocrystal Form O of the present invention is characterized by having an X-ray powder diffractogram that comprises further characteristic peaks at 16.2 and 18.1±0.3 degrees 2 theta at a Cu-Kα radiation, λ=1.5406 Å.

The XRPD diffractogram of Form O (E85-2-125) corresponded to FIG. 1—i.e. with same characteristic peaks just with different peak intensities.

The $^1$H-NMR spectrum of Form O (FIG. 2) shows a 1:2 ratio, APO FB·palmitic acid.

Figure 2:
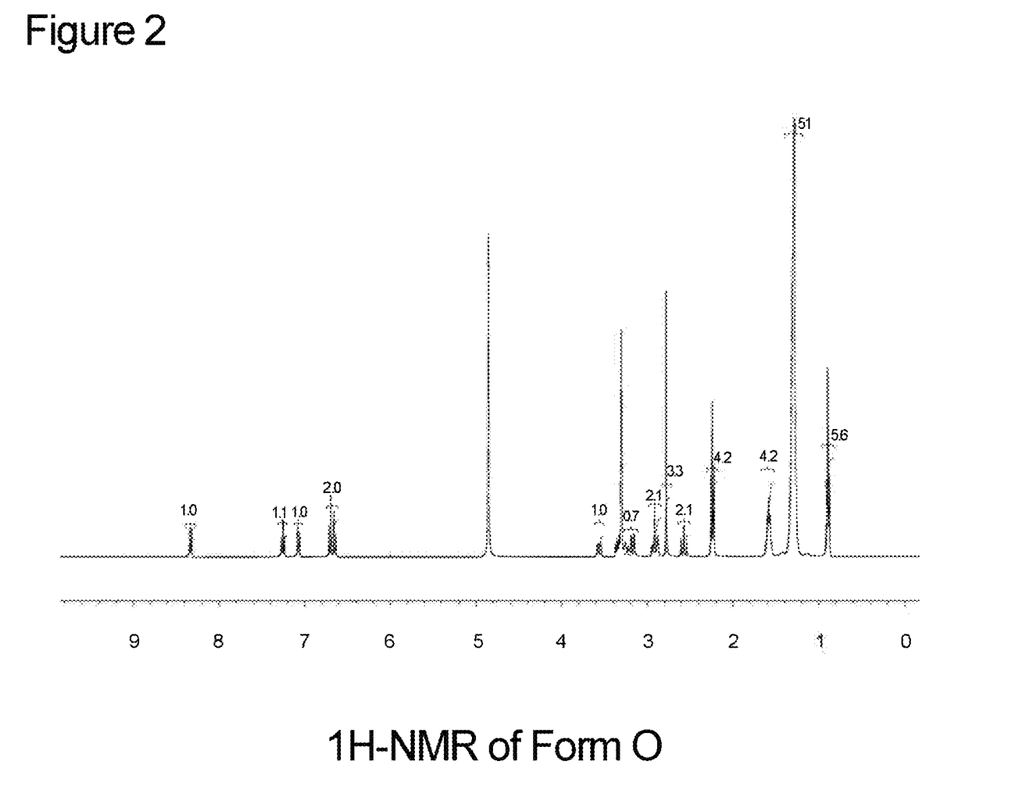
FIG. 2: The $^1$H-NMR spectrum of Form O (FIG. 2)—it shows a 1:2 ratio, APO FB·palmitic acid. For further details see Example 2 herein.

The $^1$H-NMR spectrum of Form O (E85-2-125) corresponded to FIG. 2.

1H-NMR of pure Form O (FIG. 2) indicated that the ratio APO·palmitic acid is 1:2. Without being limited to theory—it is therefore believed that Form O is an ionic cocrystal: the first palmitic acid forms a salt with APO and the second palmitic acid forms the cocrystal with this salt.

Example 3: Experimental Procedure for "Form P" Preparation: Apo·Palmitic Acid (1:7)

Preparation of Form P (E85-2-049)

In a 10 mL round-bottomed flask, APO FB (300 mg, 1.12 mmol) and palmitic acid (288 mg, 1.12 mmol, 1 eq) were suspended in EtOAc (3 mL, 10 V). The mixture was heated to reflux before cooling slowly to room temperature. Then, the resulting slurring was stirred overnight at RT, and then, at 0-5° C. (ice bath) for 2 h.

The solid was filtered with a sintered funnel (porosity 3), washed with EtOAc (2×0.3 mL, 2×1 V) and dried under vacuum (approx. 1 mbar, RT, overnight) giving Form P (79 mg, 14%) as a light brownish solid.

Characterization of Form P (E85-2-049)

Figure 3:
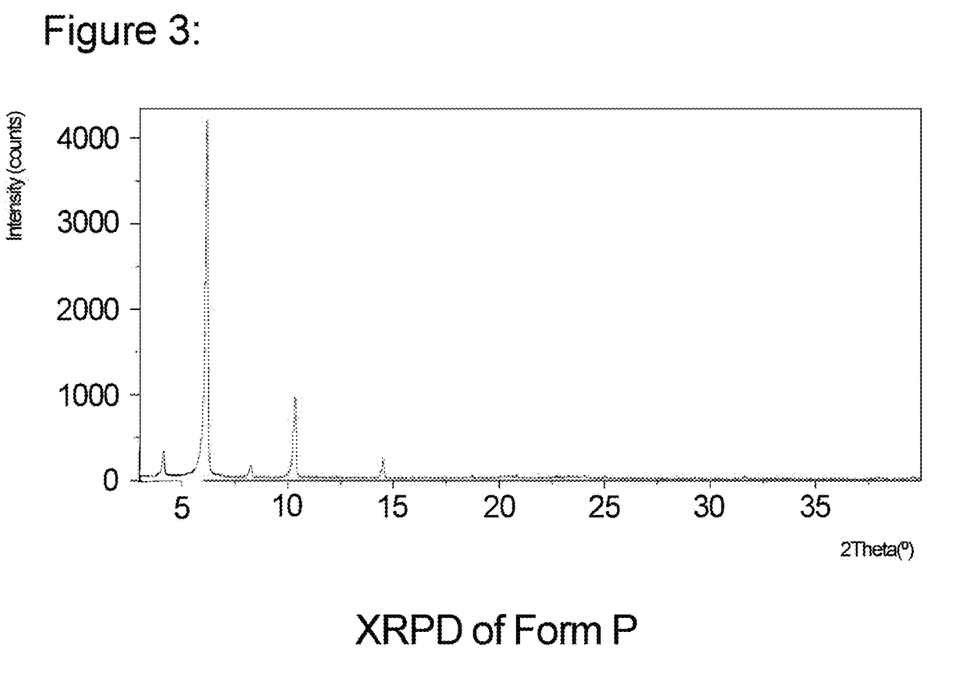
FIG. 3: The XRPD diffractogram of Form P APO·palmitic acid it shows a good crystallinity. For further details see Example 3 herein.

The XRPD diffractogram of Form P (E85-2-049) is shown in FIG. 3 it shows a good crystallinity.

Characteristic Peaks are at 6.2° 2θ:

The cocrystal Form P of the present invention is characterized by having an X-ray powder diffractogram that comprises characteristic peaks at 4.1, 6.2 and 10.3±0.3 degrees 2 theta at a Cu-Kα radiation, λ=1.5406 Å.

Figure 4:
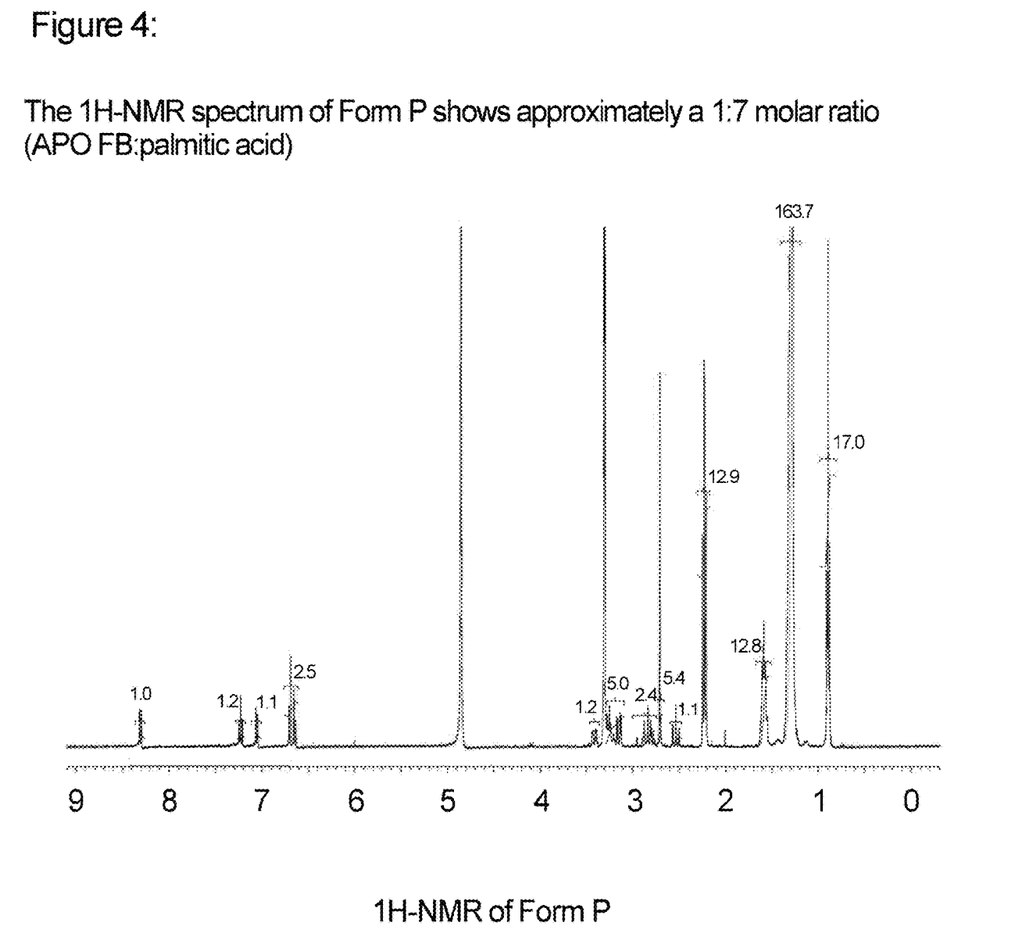
FIG. 4: The $^1$H-NMR spectrum of Form P—it shows approximately a 1:7 molar ratio (APO FB:palmitic acid).

The $^1$H-NMR spectrum of Form P (FIG. 4) shows approximately a 1:7 molar ratio (APO FB·palmitic acid).

Example 4: Evaluation of Apo-Palmitic Acid Solid Forms of the Invention

Solubility in Water

Water was progressively added at RT to APO HCl (I) until complete dissolution was reached. Subsequently, the same volume of water was added at RT to the other salts in order to compare their solubility. The mixtures were stirred for 10-15 minutes to allow equilibration. As the salts remained insoluble, the suspensions were diluted with twice the original volume and allowed to equilibrate for another 10-15 minutes at RT.

APO HCl (I) dissolved upon addition of 54 V of water at RT.

Palmitic acid forms of the invention, as a mixture of Form O+Form P (see Examples above), not soluble in 108 V of water at RT.

Accordingly, APO·palmitic acid solid forms of the invention are essentially insoluble in water this is contrary to APO HCl, which is soluble in water.

Stability

The stability of the APOPALMITIC ACID solid Form O (see Example above) was initially studied under accelerated storage conditions 40±2° C./75±5% RH (according to ICH guidelines) for 1 week.

The results showed that Form O remained stable over 1 week under accelerated conditions.

Example 5: Comparative Kinetic Solubility Study—APO-Palmitic Acid Solid Form of the Invention was the Best As discussed herein, an objective of the present invention is to developing a slow release formulation of apomorphine i.e. a significant less soluble form than APO HCl (I).

A comparative kinetic solubility study of APO HCl (I) was performed in water at 37° C. with the selected crystalline forms:

Form F (benzoic acid salt) made reference salt
Form M (adipic acid salt) made reference salt
Form J (sulfuric acid salt) made reference salt
Form O (palmitic acid cocrystal of the invention see Example above)

Note: As pure Form O was not available for this kinetic solubility study of this Example, a mixture of Form O+P was used to obtain a first approximation. Without being limited to theory, the present inventors do not believe there is a significant difference between Form O and Form P in relation to the kinetic solubility study of this Example.

The crystalline forms were separated from the aqueous medium (containing an antioxidant agent: ascorbic acid) by a dializing membrane with the aim to simulate subcutaneous injections. The relative solubility of APO was obtained by comparison of the APO peak area in the HPLC analyses of the mother liquors.

Experimental Procedure

The solubility tests were performed in a minireactor HME-R provided with a 500 mL vessel, a temperature sensor and mechanical stirring. APO HCl (I), Form F, Form M, Form J and Form O were previously ground in a mortar in order to minimize the particle size effect (no crystalline transformation took place as confirmed by XRPD).

The weight corresponding to 200 mg of APO FB of each material and 2 mL of an aqueous 0.05% ascorbic acid solution were introduced in a dialysis tube of 17 cm (cellulose membrane with a typical molecular weight cut-off=14,000, Sigma-Aldrich D9777-100FT) containing a glass ball to prevent the dialysis tube from floating. The dialysis tube was suspended in an aqueous 0.05% ascorbic acid solution (500 ml) at 37° C. without stirring (FIG. 27) and the minireactor was covered with an aluminium foil to prevent it from light. Aliquots of ca. 1 ml of the aqueous solution were taken at different times after stirring the solution at 100 rpm for 1 minute (the dialysis tube was separated from the solution during the stirring). The aliquots were filtered through a 0.20 μm nylon filter and directly analyzed by HPLC.

The following HPLC conditions were used:
Column: Zorbax Eclipse XDB-C18, 150×4.6 mm, 5 μm
Mobile phase: HCOOH 0.1% aq/ACN (95:5)-10 min-(50:50)-5 min-(50:50) Post time 5 min
Temperature: RT
Flow rate: 1 mL/min
Wavelength: 220 nm
Injection: 5 μL
Run time: 15 min Results The kinetic solubility study of the selected APO forms was performed at 37° C. in water in the presence of ascorbic acid (0.05% w/w) to avoid degradation and compared with APO HCl (I). In order to simulate subcutaneous injections, the solid was introduced in a dialysis bag. The kinetic profile of all the tested APO forms indicates a slower APO release in the medium than that of APO HCl (I). However, the best profile was obtained with the APO·palmitic acid solid form of the invention.

FIG. 5 shows the result of the comparison of kinetic solubility profile of the different studied crystalline APO salts. The mentioned "APO solvate" in the figure was a very minor (w/w) impurity.

As can be seen—the APO·palimitic acid solid Form O of the invention had a significant slower solubility rate as compared to any of the other testes salts.

With respect to APO·palmitic acid solid of the invention it is here also relevant to note:

Due to the very low solubility of Form O in the medium, the solubility reached saturation after 4 days before complete dissolution of palmitate salt.

In order to simulate an open system, the aqueous 0.05% ascorbic acid solution was changed every 3 days in order to observe the complete release of APO in the medium by dissolution or dissociation of Form O.

A complete release of APO FB seems to be observed after about 3 weeks. This release is clearly slower than APO HCl (I) and the other APO salts used in this study.

The present inventors have also tested other herein relevant possible suitable APO—none of these other tested salts had a slower solubility rate than APO·palmitic acid solid form of the invention.

Conclusions

As discussed above, the APO·palmitic acid solid form of the invention had a significant slower solubility rate in aqueous media as compared to any of the other tested salts (see e.g. FIG. 5).

Accordingly, an APO·palmitic acid solid form of the invention may be considered as the most promising crystalline form for a slow release formulation due to its slower solubility rate in water.

Further, an APO·palmitic acid solid form of the invention is believed to have a low toxicity a reason for this relates to the very low toxicity of palmitic acid as such.

Example 6: In Vivo Comparative Pharmacokinetic Study—Apo-Palmitic Acid Solid Form of the invention was the Best As discussed herein, an objective of the present invention is to develop a slow release formulation of apomorphine—i.e. a significant less soluble form than APO HCl (I).

An in vivo comparative pharmacokinetic study of APO HCl (I) was performed in rats by subcutaneous administration with the selected crystalline forms:

Form O (palmitic acid cocrystal of the invention see Example above)

Note: Pure Form O was used in this study

Experimental Procedure

Form O was administered subcutaneously to Sprague Dawley rats, three times (every other day) over six days (total of three 0.6-mL administrations). Apomorphine Hydrochloride (Apo-HCl) was administered subcutaneously to Sprague Dawley rats three times a day for six days (total of eighteen 0.1-mL administrations). Both test items were compared for tolerance and systemic exposure: blood samples were collected from the lateral vein of the tail from all animals on treatment days 1 and 5 at all groups from main animals, samples were analyzed for apomorphine level determination.

| Test Item | Groups | | |
|---|---|---|---|
| | 1 Control (Vehicle D1) | 2 APO-HCl | 3 APO-palmitic acid solid form |
| Dose levels (mg/animal) | 0 | 1.5 | 7.8 |
| Administration volume | 0.6 | 0.3 | 0.6 |
| Main Animals | 6M + 6F | 6M + 6F | 6M + 6F |

Results

Figure 6:
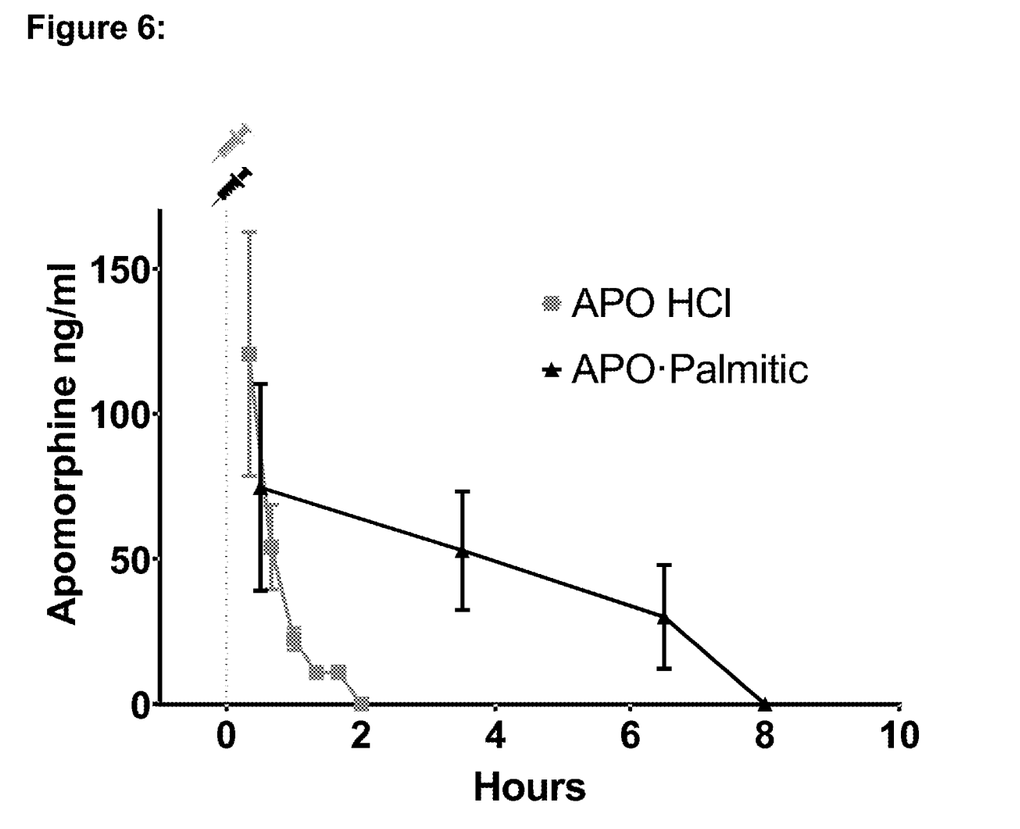
FIG. 6 shows the result of the comparison of in vivo pharmacokinetic profile of Apomorphine HCl and APO·palmitic subcutaneously administered to rats—it demonstrates that an APO·palmitic solid form of the invention has a surprising significant higher sustained release than Apomorphine HCl.

FIG. 6. Cmax and PK profile differ from one test item to the other. APO·palmitic acid solid form of the invention has Cmax values lower than Apo-HCl and AUC values higher than Apo-HCl.

Similar clinical signs were observed when comparing APO·palmitic acid solid form of the invention administered subcutaneously to Sprague Dawley rats three times (every other day) over six days and Apomorphine Hydrochloride (Apo-HCl) administered subcutaneously to Sprague Dawley rats three times a day for six days.

Conclusions

Sustained Apomorphine levels in blood were observed for APO·palmitic acid solid form of the invention vs a rapid decrease of Apomorphine levels for Apo-HCl.

REFERENCES

1: WO2015/197839A1 (Institut De Recerca Contra La Leucemia Josep Carreras)
2: WO2016/103262A2 (Neuroderm Ltd)
3: WO02/39879A2: (TAP Holdings, Inc.)
4: WO2004/082630A2 (Neurohealing Pharmaceuticals, Inc.)
5: Schultheiss et al. ("Pharmaceutical Cocrystals and Their Physicochemical Properties"; Crystal Growth & Design, Vol. 9, No. 6, 2009, p. 2950-2967)

The invention claimed is:

1. A pharmaceutical composition comprising pharmaceutically acceptable excipient(s) and comprising apomorphine (APO) in a solid crystalline form, wherein the solid crystalline form is an APO·palmitic acid cocrystal solid particle crystalline form.

2. The pharmaceutical composition of claim 1, wherein the cocrystal is an ionic cocrystal.

3. The pharmaceutical composition of claim 1, wherein at least 20% (prefera-bly at least 40%, more preferably at least 60%, even more preferably at least 80% and most at least 90%) of APO of the composition (w/w of APO as such) is an APO·palmitic acid cocrystal solid particle crystalline form.

4. The pharmaceutical composition of claim 1, wherein the average particle size of the APO·palmitic acid cocrystal solid particle crystalline form is an average par-ticle size of from 100 nm to 10 μm, measured by laser diffraction.

5. The pharmaceutical composition of claim 1, wherein the ratio APO·palmitic acid is a ratio from 1:2 to 1:15 (such as e.g. a ratio from 1:2 to 1:8).

6. The pharmaceutical composition of claim 5, wherein the ratio APO·palmitic acid is a ratio 1:2.

7. The pharmaceutical composition of claim 1, wherein the APO·palmitic acid solid particle crystalline form is Form O with X-ray Powder Diffraction (XRPD) diffractogram corresponding to the XRPD diffractogram of FIG. 1 herein, where characteristic peaks include characteristic peaks at 5.8, 8.6 and 11.5±0.3 degrees 2 theta at a Cu-Kα radiation, λ=1.5406 Å.

8. The pharmaceutical composition of claim 1, wherein the pharmaceutical composition is a tablet, a gel, a suspension, a solution, a liposome, or encapsulated in polymers.

9. The pharmaceutical composition of claim 8, wherein the pharmaceutical composition is a sus-pension.

10. The pharmaceutical composition of claim 9, wherein the suspension is a suspension wherein the APO·palmitic acid cocrystal solid particle crystalline form is suspended in an aqueous medium.

11. The pharmaceutical composition of claim 9, wherein the suspension is a sus-pension for subcutaneous injection.

12. The pharmaceutical composition of claim 1, wherein the kinetic solubility at 37° C. in water in the presence of ascorbic acid (0.05% w/w) of the APO·palmitic acid solid form is slower than for APO HCl tested under the same conditions and wherein the solubility tests are performed as described in Example 5 herein.

13. A pharmaceutical composition of claim 1 for use as a medicament.

14. A pharmaceutical composition of claim 1 for use in the treatment of:
leukemia (preferably acute myeloid leukemia (AML);

Parkinson's disease;

sexual dysfunction (preferably in a patient taking antidepressant medication);

neurological function (preferably of an individual who has a brain injury); or solid tumors in a human person.

15. A method for making an APO·palmitic acid cocrystal solid particle crystalline form comprising the steps:
- (i): suspending apomorphine free base (APO FB) and palmitic acid in a suitable medium (preferably toluene) to get a suspension;
- (ii): heating to get a solution;
- (iii): cooling to get precipitation; and
- (iv): further steps (including e.g. filtering) to obtain the APO·palmitic acid cocrystal solid particle crystalline form.

* * * * *